United States Patent [19]
Jaker et al.

[11] Patent Number: 6,007,488
[45] Date of Patent: Dec. 28, 1999

[54] MEDICAL PROBE INCLUDING AN ELECTRICALLY CONDUCTIVE MEMBRANE SUITABLE FOR MEDICAL USES

[75] Inventors: Marc L. Jaker; Anna Maria Bigonzi-Jaker, both of New Brighton, Minn.

[73] Assignee: RTC, Inc., West St. Paul, Minn.

[21] Appl. No.: 09/078,186

[22] Filed: May 12, 1998

Related U.S. Application Data

[60] Provisional application No. 60/046,288, May 12, 1997.

[51] Int. Cl.$^6$ .................................................. A61B 19/00
[52] U.S. Cl. ............................................................ 600/300
[58] Field of Search ........................... 607/115, 116, 607/117, 119, 122, 126, 128; 600/372, 373, 374, 376, 380, 381

[56] References Cited

U.S. PATENT DOCUMENTS

| | | | |
|---|---|---|---|
| 4,166,469 | 9/1979 | Littleford | 607/122 |
| 4,271,847 | 6/1981 | Stokes | 607/122 |
| 4,281,660 | 8/1981 | Fujiwara | 600/375 |
| 5,044,375 | 9/1991 | Bach, Jr. et al. . | |
| 5,411,527 | 5/1995 | Alt . | |
| 5,531,717 | 7/1996 | Feliziani et al. . | |
| 5,674,272 | 10/1997 | Bush et al. . | |
| 5,676,688 | 10/1997 | Jaker et al. . | |
| 5,711,841 | 1/1998 | Jaker . | |

OTHER PUBLICATIONS

"Shocking Treatment Proposed for AIDS", 139 Science News 207 (1991).

"Effect of Short HV Pulses on Bacteria and Fungi" Mazurek, B., et al. IEEE Transactions on Dielectrics and Electrical Insulation, vol. 2 No. 3, Jun. 1995.

"Bacterial Biofilms and the Bioelectric Effect", Wellman, N., et al., Antimicrobial Agents and Chemotherapy, Sep. 1996, p. 2012–2014.

"Electrical Energy Changes Conductivity and Determines Optimal Electrotransformation Frequency in Gram–Negative Bacteria", Bowen, B., et al., Applied and Environmental Microbiology, Oct. 1992, p. 3292–3296.

"Mechanism of Electrical Enhancement of Efficacy of Antibiotics in Killing Biofilm Bacteria", Costerton, J. William, et al., Antimicrobial Agents and Chemotherapy, Dec. 1994, p. 2803–2809.

*Primary Examiner*—William E. Kamm
*Attorney, Agent, or Firm*—Snell & Wilmer

[57] ABSTRACT

A modified membrane material, including a conductive surface, which may be used for a variety of medical or other applications, is provided. Various devices can be formed of the conductive surface materials, including tubes, probes, catheters and the like. Activation of the conductive surface, such as by connection to a suitable energy source, enables electrical current to be passed into a body region or to a device (e.g., a container) useful in holding and/or treating other materials.

6 Claims, 9 Drawing Sheets

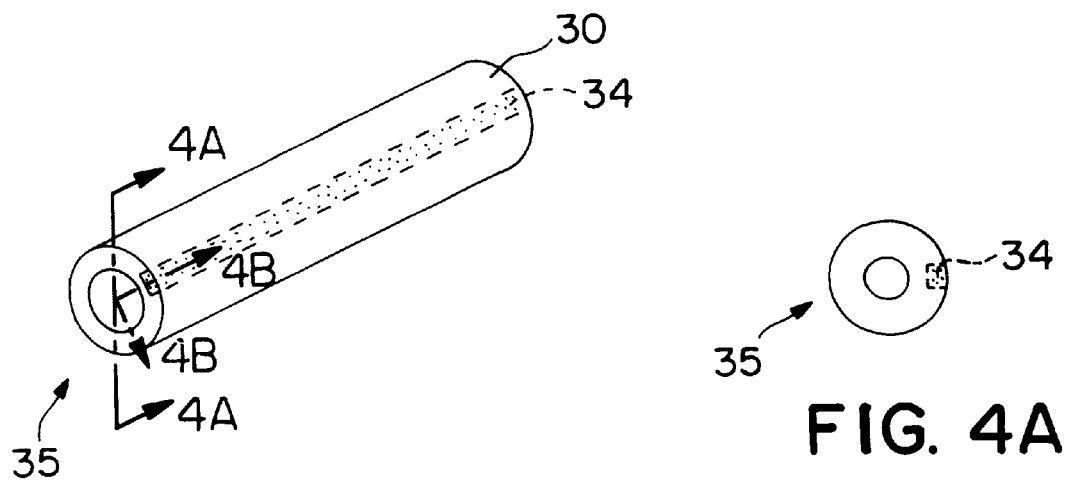
FIG. 4
FIG. 4A
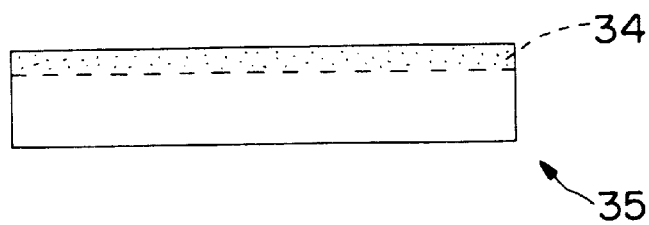
FIG. 4B
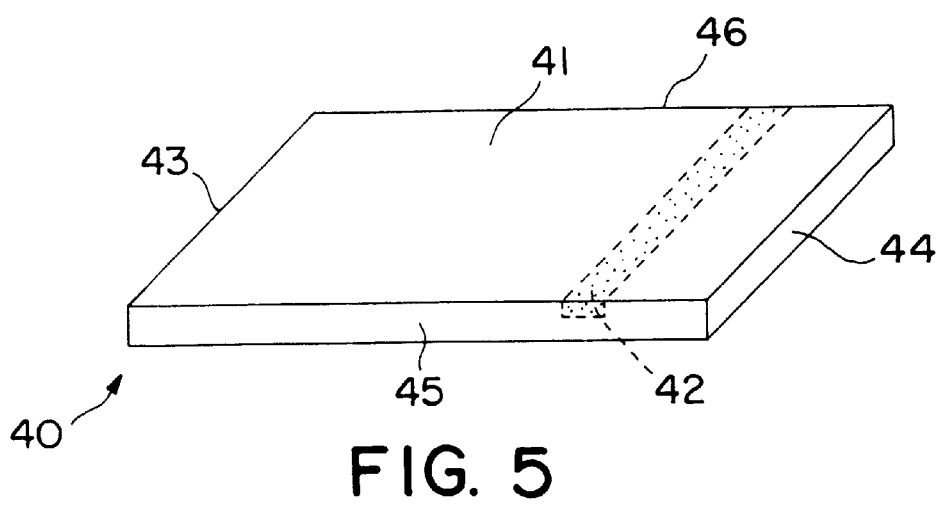
FIG. 5

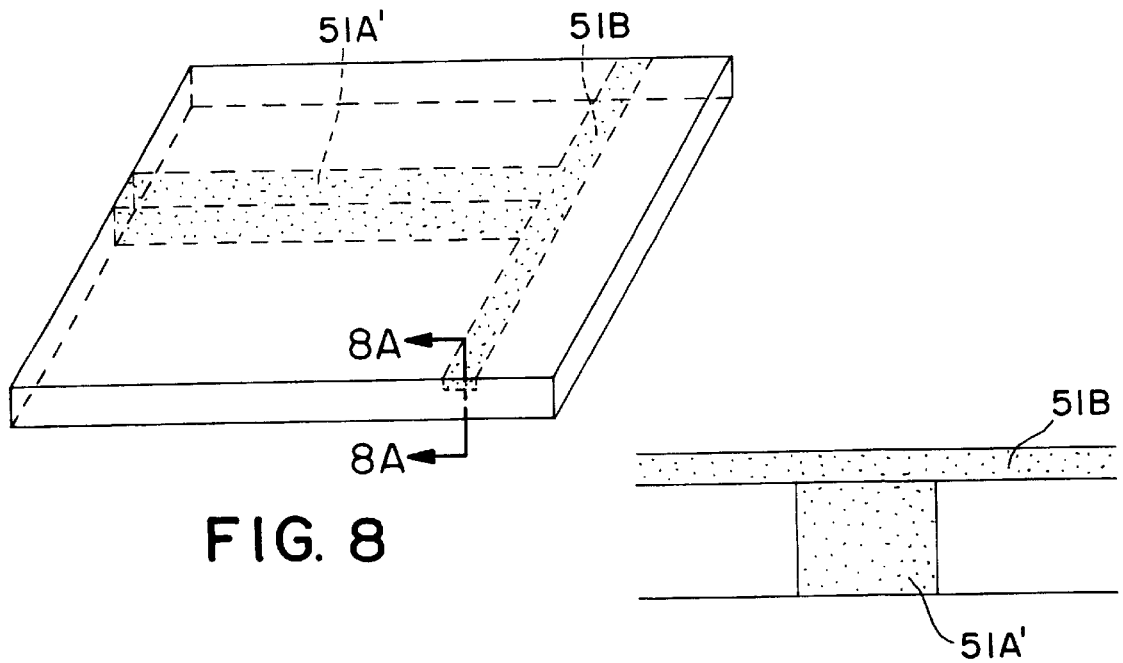
FIG. 8
FIG. 8A
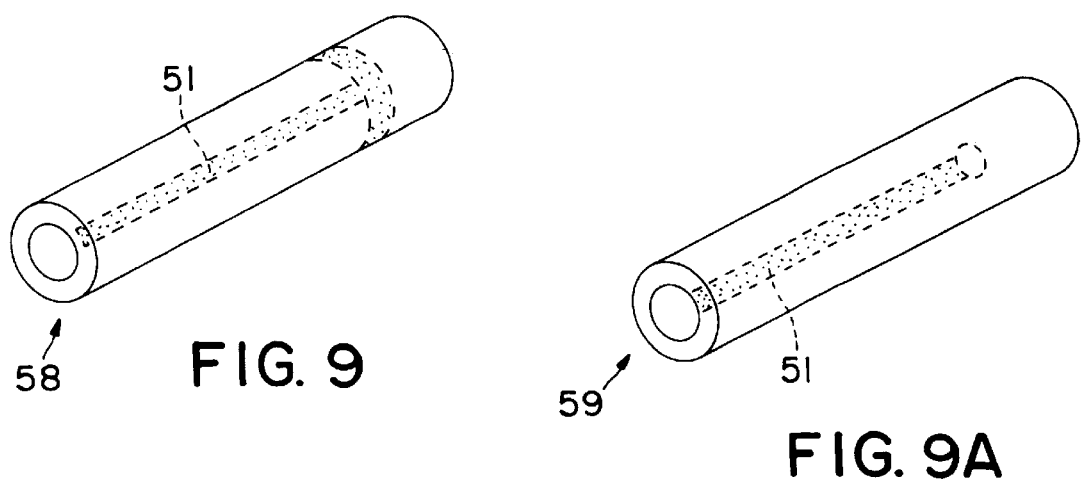
FIG. 9
FIG. 9A
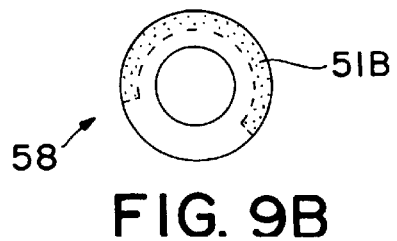
FIG. 9B

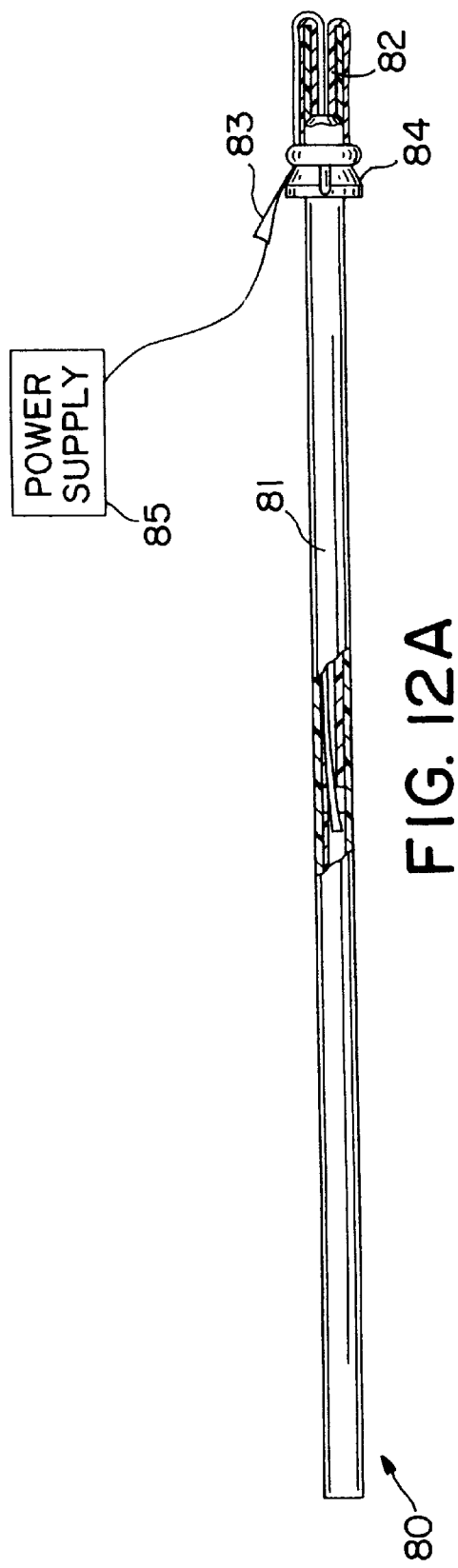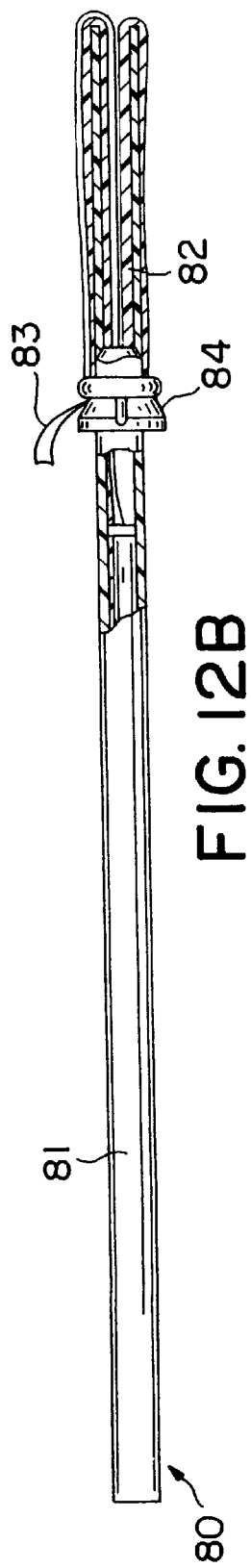

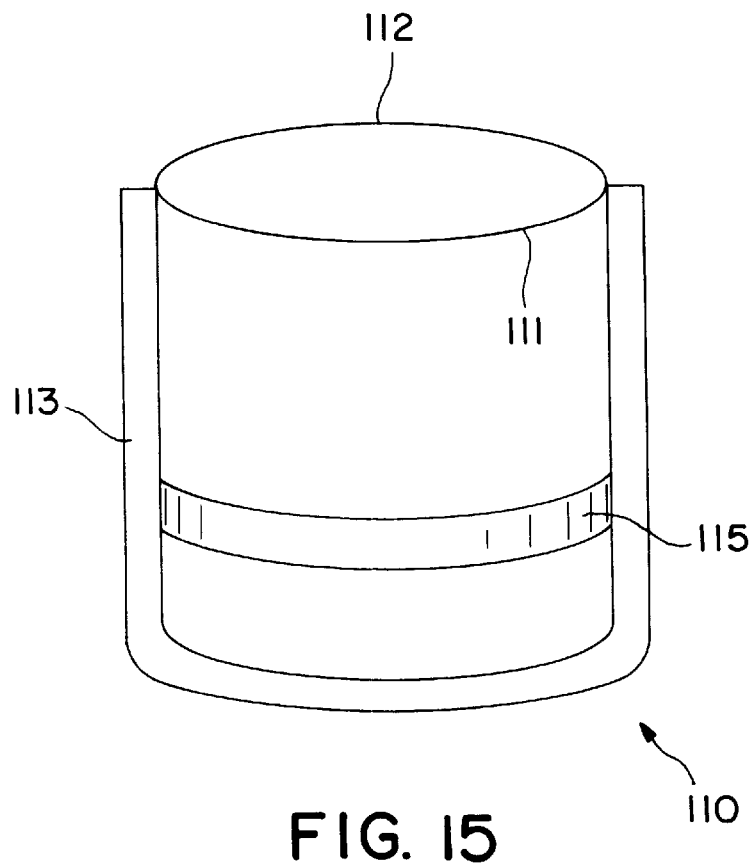
FIG. 15
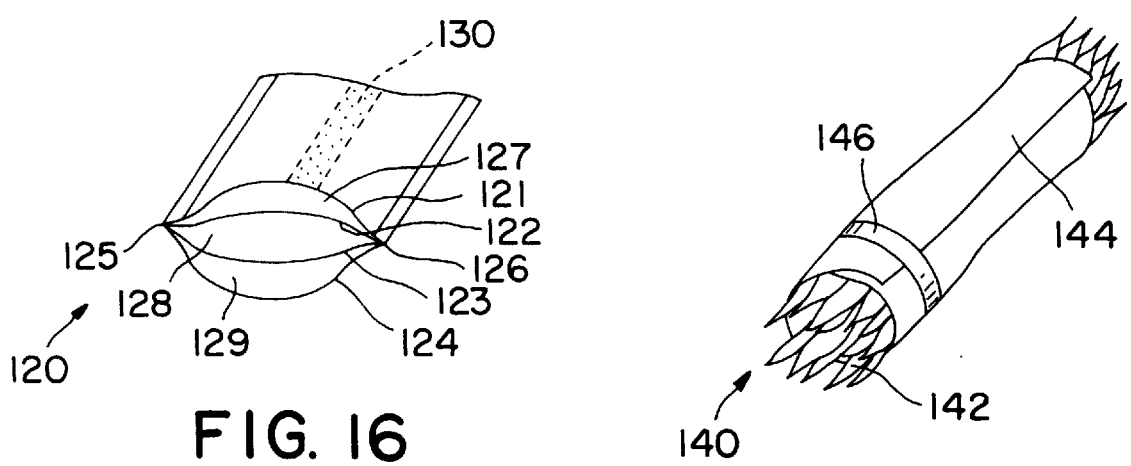
FIG. 16
FIG. 17

MEDICAL PROBE INCLUDING AN ELECTRICALLY CONDUCTIVE MEMBRANE SUITABLE FOR MEDICAL USES

CROSS-REFERENCE TO RELATED APPLICATIONS

This application claims the benefit of U.S. Provisional Application No. 60/046,288, filed May 12, 1997.

FIELD OF THE INVENTION

The present invention generally relates to membranes useful in connection with a variety of medical applications, and more particularly to membranes that include conductive material, which may be coated onto or integral to the membranes.

BACKGROUND OF THE INVENTION

Conductive surfaces have several applications in medicine. For example, cardiac pacemakers have conductive surfaces that transfer electrical pulses to the heart to stop unwanted electrical activity in the conduction fibers of the heart. Additionally, it is well known that electrical fields applied to nerves, muscles, vessels and the like can stimulate the corresponding nerves, muscles, vessels or other tissue.

Recently, new, potential, uses for the conduction of electricity in medical contexts have been developed. For example, in Shocking Treatment Proposed for AIDS. (zapping the AIDS virus with low-voltage electric current), 139 SCIENCE NEWS 207 (1991), methods to reduce infectivity of viruses by applying a current, e.g. in the range of about 50 to 100 $\mu$amps, to white blood cells containing the virus exist. The current is believed to affect the virus such that production of enzymes crucial to virus reproduction is inhibited.

Application of an electric pulse to fluids to sterilize the fluid is also known. In particular, Viazurek et al., Effect of Short HV pulses on Bacteria and Fungi, 2 EEE TRANSACTIONS ON DIELECTRICS AND ELECTRICAL INSULATION 418 (1995) discloses use of electrical pulses to sterilize consumable fluids, which may either be ingested by or inserted into a patient.

Another medical application is the electrical sterilization of biofilms (e.g., biofilms which form on a dialysis membrane away from an electrode). Wellman et al., Bacterial Biofilms and the Bioelectric Effect, 40 ANTIMICROB AGENTS CHEMOTHER 2012 (1996) discloses increased efficiency of sterilizers, such as antibiotics and biocides, by the addition of an electric field. Thus, in the presence of an effective electrical field, less sterilizer is required to kill unwanted bacteria and may therefore reduce the risk of antibiotic resistance.

Application of electrical current may also be used to simulate growth of certain bacteria. As disclosed in Using Electricity to Kill Bugs, 18 EPRI JOURNAL 4 (1993), this technique may be used for, inter alia, production of genetically engineered substances. Alternatively, this technique could be used to breed beneficial bacteria within a body. Additionally, it is thought that small electrical fields can attract or repel various pathogens or bacteria from an area which includes the electrical field.

Use of electricity to generate local heat is also known. In this regard, application of localized heat within a body can have a therapeutic effect. Accordingly, placing resistive or conductive materials within the body and passing a current through such materials to generate heat to the body region of interest can have therapeutic value. In addition, extreme local heat may be used to cauterize or remove unwanted material. Removal of unwanted material is assisted by destroying, burning, or reducing a volume of unwanted material, making removal of such material through a relatively small opening possible. For example, unwanted plaque or cholesterol may be removed using this technique.

The above and other medical applications generally are accomplished by electrically connecting sensors inside a body to instruments outside a body, or by the invasive insertion of rigid electrodes into a patient, or by the addition of electricity to a device, such as a container, filled with a material to be treated. Each of these methodologies have various drawbacks.

For example, invasive insertion of rigid electrodes is problematic because, inter alia, the insertion may increase the risk of infection to the patient. Additionally, insertion of a rigid electrode may cause discomfort to the patient during and/or after insertion.

Similarly, medical applications involving the external use of electricity (for example, to grow or inhibit growth of certain bacteria) often require multiple components, for example, an electrode which is attached to a device (e.g., a container) to hold the material to be treated. As a result, the apparatus is typically complex and, because of the extra components, extra surface area must be sterilized prior to use, thus, tendering increased costs associated with the procedure.

SUMMARY OF THE INVENTION

The present invention provides a biocompatible medical device having a flexible, conductive membrane which addresses the aforementioned drawbacks of presently known conductive surfaces used for medical application of electricity to a body or other material to be treated.

While the way in which the present invention addresses the drawbacks of the prior art will be described in greater detail below, in general, in accordance with various aspects of the present invention, a conductive surface is provided which can be formed into a variety of different devices. In its broadest sense, however, the present invention relates to the conductive surface and the manner by which such a surface is formed.

In accordance with various aspects of the present invention, such a surface is formed by application of a conductive material by deposition, impregnation and/or mechanical attachment to a flexible substrate. This material can then be formed into a variety of devices ranging from a conductive sheet, a conductive tube, probes, catheters and the like.

In accordance with various aspects of the present invention, the flexible substrate preferably comprises a polytetrafluoroethylene (PTFE) resin or a modified PTFE resin. In addition, preferably, the conductive material comprises a metal.

In accordance with another aspect of the present invention, a probe for insertion into a body orifice is provided. The probe comprises a tube, a modified PTFE membrane, a conductive surface and a guide assembly. The membrane and conductive surface are suitably attached to the guide assembly and inverted over the first open end of the probe with the majority of the membrane being contained within the lumen of the tube. When the probe is inserted into a body orifice, the membrane and conductive surface are withdrawn from the tube open end and the membrane and conductive surface are interposed between the tube and the body orifice.

BRIEF DESCRIPTION OF THE DRAWING FIGURES

A more complete understanding of the present invention may be derived by referring to the detailed description and claims when considered in connection with the Figures, where like reference numbers refer to similar elements throughout the Figures, and:

FIG. 4 is a perspective view showing the surface of FIG. 3 as it has been formed into a tube-like device;

FIG. 4A is an end view of the tube of FIG. 4 taken along the lines A—A of FIG. 4;

FIG. 4B is a cross-sectional view of the tube of FIG. 4 taken along the lines B—B of FIG. 4;

FIG. 5 is a perspective view of a further embodiment of a conductive surface in accordance with the present invention;

FIG. 8 is a perspective view of a still further embodiment of a conductive surface in accordance with the present invention;

FIG. 8A is a cross-sectional view of a conductive surface of FIG. 8;

FIG. 9 is a perspective view of a tube formed of the conductive surface of FIG. 7;

FIG. 9A is a perspective view of a further embodiment of a tube formed of the conductive surface of FIG. 7.

FIG. 9B is a cross-sectional view of still a further embodiment of a tube formed of a conductive surface in accordance with the present invention;

FIG. 12A shows a probe for insertion into a body orifice including an unfolding membrane provided with a conductive surface in accordance with the present invention;

FIG. 12B shows a further view of the probe of FIG. 12A showing the unfolding of the conductive surface and membrane;

FIG. 15 is a perspective view of a pouch formed of a plurality of conductive surfaces in accordance with the present invention;

FIG. 16 is a perspective view of a multi-lumen tube formed of at least one conductive surface in accordance with the present invention;

FIG. 17 is a perspective view of a conductive surface in accordance with the present invention utilized as a stent covering;

DETAILED DESCRIPTION OF PREFERRED EXEMPLARY EMBODIMENTS

The present invention relates generally to devices, which can be formed from flexible materials having at least one conductive surface, which devices may be useful in various medical applications. Such applications include a variety of medical procedures, applications, and thus, the devices of the present invention can be used for internal and/or external procedures to a body or for treatment of other materials. For example, devices in accordance with various aspects of the present invention may be used to apply localized heat or an electrical field to a particular region of a body or other material to be treated.

Figure 1:
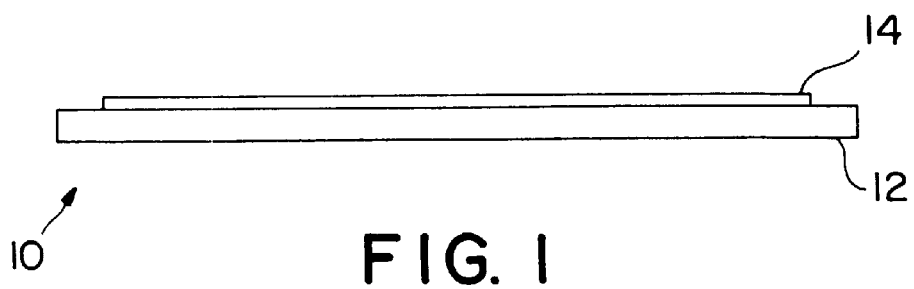
FIG. 1 is a side view of a conductive surface in accordance with one embodiment of the present invention.

Referring now to FIG. 1, a conductive surface 10 in accordance with one aspect of the present invention is shown. Surface 10 suitably includes a flexible material 12 which is configured to receive a conductive path 14. Preferably, path 14 covers at least a portion of material 12. As described in greater detail hereinbelow, surface 10 is configurable to be formed in a variety of geometric configurations to form a device, which device may be suitable for various medical applications.

Flexible material 12 may include any material which is biocompatible and capable of receiving conductive path 14, yet which is flexible enough to perform the desired functions. As such, the materials which can be utilized in the context of the present invention to form flexible material 12 can vary from application to application. However, in accordance with a preferred aspect of the present invention, flexible material 12 comprises a polytetrafluoroethylene (PTFE) resin, a modified PTFE resin or combinations thereof. In accordance with a particularly preferred aspect of the present invention, material 12 is preferably formed from a sintered PTFE film formed by skiving it off a billet to a desired thickness. Preferable PTFE billets may comprise Hoechst TMF 1700 or TMF 1702, or other chemical compounds available from DeWall Industries of Saunderstown, R.I. under the names DW/200 and DW/220, respectively, or under other names as may be obtained from other processors. Such materials typically comprise a modified PTFE resin, which includes a PTFE polymer modified by the addition of a small amount of perfluoro propyl vinyl ether (PPVE). Other modified PTFE resins, such as those available from DuPont under the name Mitsui-DuPont TG 70-J, may also be utilized. Preferably, the modified PTFE resins include less than about 5 wt % PPVE. Additionally, PTFE homopolymers or copolymers with comonomers like PPVE, PFA and the like may be used in the context of the various aspects of the present invention. In general, it should be appreciated that other PTFE films and/or resins, as are now known or hereafter devised by those skilled in the art may also be used to form devices in the context of the present invention.

In general, the aforementioned PTFE resin films are such that interfacial fusion is possible; that is, as will be appreciated by those skilled in the art, the materials can be heat sealed upon themselves. As will be described in greater detail hereinbelow, the flexible materials useful in the context of the present invention are suitably formed into devices which can be utilized in various medical applications. Such materials, which can be used to form flexible material 12, may be processed as set forth in, for example, U.S. Pat. No. 5,711,841 issued Jan. 27, 1998, to Jaker, or the related U.S. Pat. Nos. 5,531,717 issued Jul. 2, 1996 to Feliziani et al., and/or 5,676,688 issued Oct. 14, 1997 to Jaker et al. The entire contents of each of the '841, the '717 and the '688 patents are hereby incorporated into this application by this reference. Such processing may include, for example, elongation, tensilization, sintering, etc.

With continued reference to FIG. 1, conductive path 14 in accordance with various aspects of the present invention is preferably applied to material 12. Such application may be accomplished through a variety of methodologies. For example, path 14 may be deposited upon material 12. Alternatively, path 14 may be adhered to material 12 in any conventional fashion as is now known or hereafter devised by those skilled in the art. In this regard, natural attachment of path 14 to material 12 may be accomplished by virtue of the chemical and/or mechanical composition of the components. For example, static or other adhesive forces may be sufficient in certain instances to secure the material which comprise path 14 to flexible material 12.

In general, preferably conductive path 14 is formed of a material which enables electrons to be conducted therewithin. In this regard, conductive path 14 suitably comprises any electrically conductive material such as metals, combinations of metals and/or the like. In accordance with the preferred aspect of the present invention, and with continued reference to FIG. 1, conductive path 14 is formed of a material which comprises gold, silver, copper, nickel, zinc or any combinations thereof.

With continued reference to FIG. 1, path 14 may be suitably deposited onto flexible material 12. In accordance with preferred aspects of this embodiment of the present invention, conductive path 14 is formed by vapor coating, plasma coating, sputter coating, ion coating, and/or wet plating a desired conductive material (e.g., a metal) onto flexible material 12. For example, conductive path 14 may be formed on flexible material 12 by applying an electrical bias to or proximate material 12 and causing conductive ions (e.g., metal ions) to deposit onto material 12. As will be appreciated by those skilled in the art, application of such an electrical bias during deposition of the material forming path 14 may increase adhesion between path 14 and flexible material 12, etc.

Preferably materials selected for use as flexible material 12 comprise, as previously noted, a biocompatible material. Such materials generally have a composition which may include micro fissures or cracks, the presence of which aid in bonding between flexible material 12 and conductive path 14.

In alternative embodiments of the present invention, some of which will be described in greater detail hereinbelow, conductive path 14 may be applied to material 12 using a snap ring, or sandwiching conductive layer 14 between two layers of flexible material 12, etc.

With continued reference to FIG. 1, flexible material 12 may be suitably prepared for deposition of conductive material to form path 14 in a variety of ways, as will be appreciated by those skilled in the deposition art. For example, in accordance with a preferred embodiment of the present invention, material 12 is treated with an etchant such as Gore Tetra-Etch®, is then preferably rinsed with isopropyl alcohol and distilled or deionized water to, among other things, remove fluorine residue from a surface of material 12, and is then dried prior to conductive material deposition. To promote adhesion, the treatment, rinse, and deposition processes are preferably performed in a clean environment and away from excess ultraviolet light.

In accordance with various aspects of the present invention, flexible material 12 preferably has a thickness on the order of less than 0.005 inches thick. As will be described in greater detail below, membranes/layers of such a thickness can be easily formed into a variety of suitable devices useful in a variety of medical applications. It should be appreciated, however, that conductive surface 10 may have thickness in excess of 0.005 inches. However, preferably the thickness of conductive surface 10 is in the range from about 0.0005 inches to about 0.005 inches. With continued reference to FIG. 1, in accordance with this embodiment of the present invention, conductive path 14 formed by a deposited layer preferably has a thickness in the range of about 10 to 100 angstroms.

Figure 2:
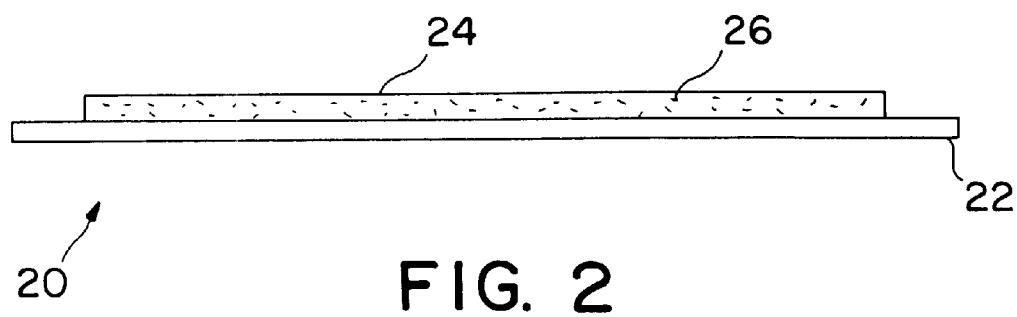
FIG. 2 is a side view of a further embodiment of a conductive surface in accordance with the present invention.

Referring now to FIG. 2, a conductive surface 20 includes a flexible membrane 22, which is configured for receipt of a conductive layer 24. In accordance with this alternate embodiment of the present invention, conductive layer 24 includes suitably a plurality of particles of conducting material 26, such that layer 24 is conductive. As will be described hereinbelow, layer 24 may be used alone or in connection with flexible membrane 22, such as is shown in FIG. 2. When used in connection with membrane 22, layer 24 may be affixed to membrane 22 using any suitable means. In accordance with preferred aspects of this embodiment of the present invention, layer 24 is attached to membrane 22 by spot welding the layers together. Other mechanical or chemical attachment mechanisms or devices may, however, also or in the alternative, be used.

In accordance with preferred aspects of this embodiment of the present invention, flexible membrane 22 may include any biocompatible, flexible material that can receive flexible membrane 22, such as by spot welding. For example, the aforementioned PTFE resins may be used to form conductive layer 24. Materials or surfaces formed of such resins are substantially biocompatible, and the material or surface can be impregnated with conducting material 26 if desired.

Preferably, and as will be described in greater detail below, layer 24 comprises a modified PTFE resin of the type previously described which is impregnated with suitable conducting material. In the context of this embodiment of the present invention, preferably layer 24 is fully impregnated with the conducting material. Stated in another way, conducting material 26 is fully dispersed throughout layer 24 such that, in general, layer 24 is fully conducting. As will be appreciated, and as will be described in greater detail below, in accordance with various other aspects of the present invention, portions of layer 24 may be formed to be conducting such as by impregnating the PTFE resin making up layer 24 about only a portion of the layer. Conductive material 26 may be any material that enables electricity to be conducted through a portion of layer 24. Preferably, conducting material may include particles of metal, carbon and/or the like. Iron or iron-like particles have been found to be particularly preferred.

Figure 3:
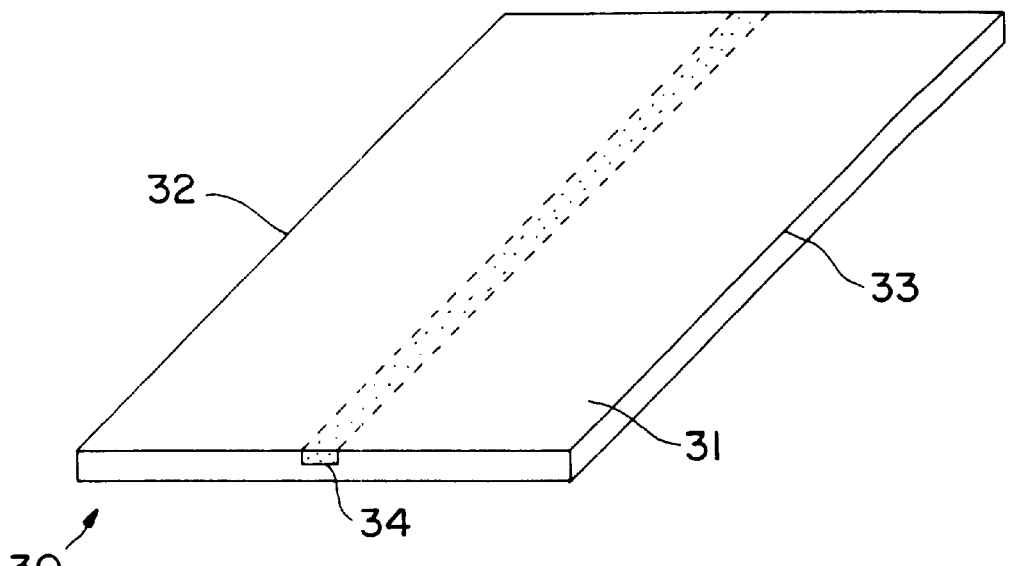
FIG. 3 is a perspective view of yet a further embodiment of a conductive surface in accordance with the present invention.

For example, with reference now to FIG. 3, a conductive surface 30 may be provided which includes a flexible substrate 31 having a first edge 32 and a second edge 33. Substrate 31 is suitably provided with a conductive path 34 which spans the length of substrate 31 between respective edges 32 and 33. Conductive path 34 may be suitably formed in substrate 31 such as by impregnation. In this regard, and as shown best in FIG. 3, conductive particles may be impregnated into a portion of substrate 31 through the use of any conventional or hereafter devised impregnation technique. Preferably, as shown in FIG. 3, impregnation of conductive materials in this fashion causes only a portion of one of the sides of substrate 31 to exhibit conductive path 34. It should be appreciated, however, that such conductive path could span the thickness of substrate 31, or alternatively, span various depths between the surface impregnation generally shown in FIG. 3 to the entirety of the thickness of substrate 31.

Referring now to FIGS. 4–4A, a conductive surface 30 is suitably configurable to form a tube 35. As will be appreciated, tube 35 may be formed in a variety of ways. For example, edges 32 and 33 may be attached using an appropriate adhesive, spot welding or the like. Preferably, tube 35 is formed by joining edges 32 and 33 and forming a heat seal at the junction by applying heat proximate or directly to the junction of edges 32, 33. Tube 35 includes a conductive path 34 spanning the length of tube 35. In accordance with a further preferred aspect of this embodiment and as shown, for example, in FIG. 4A, path 34 suitably spans all or most of the length of tube 35. As previously noted, in accordance with a preferred aspect of this embodiment of the present invention, conductive path 34 extends only partially into flexible substrate 31.

Tube 35, as so configured, suitably enables the conduction of electricity through conductive path 34, when conductive path 34 is suitably connected to an appropriate power supply (not shown). Suitable power supplies may include voltage, current or other electrical generating sources.

It should be appreciated that various configurations of conductive surfaces can be formed in the context of the present invention. For example, and referring now to FIG. 5, a conductive surface 40 may suitably comprise a flexible substrate 41 incorporating a widthwise oriented conductive path 42. In accordance with various aspects of this embodiment of the present invention, flexible substrate 41 is suitably provided to exhibit respective ends 43, 44 and respective edges 45, 46. Preferably, as show, conductive path 42 traverses between ends 43 and 44.

Figure 6:
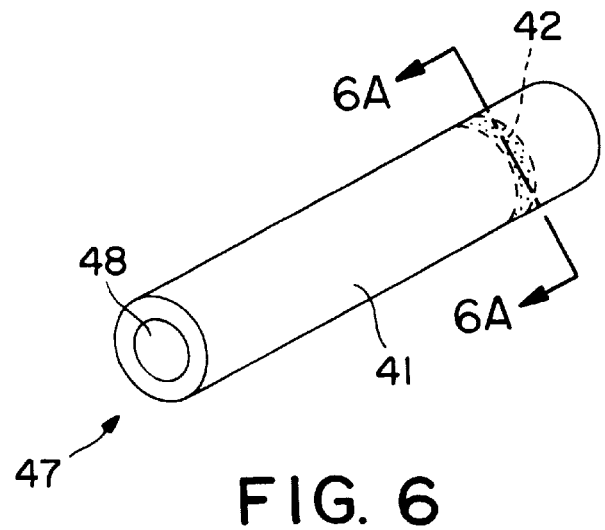
FIG. 6 is a perspective view of a tube which has been formed from the conductive surface of FIG. 5.
Figure 6A:
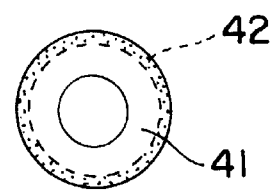
FIG. 6A is a cross-sectional view taken along the lines A—A of FIG. 6.
Figure 6B:
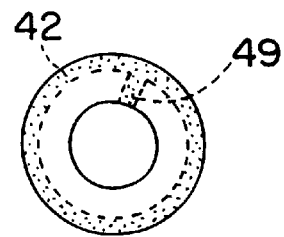
FIG. 6B is a cross-sectional view of a tube in accordance with another embodiment of the present invention.

Conductive surface 40, like conductive surfaces 30, 20 and 10, is suitably configurable to form a suitable device. For example, and with reference now to FIG. 6, surface 40 may be suitably formed into a tube 47. For example, edges 45 and 46 may be suitably joined to form tube 47. As noted above, edges 45 and 46 may be attached in a variety of ways, and are preferably attached to each other by heat sealing edges 45, 46 together. Tube 47, as shown, includes a circumferential conductive path, namely, conductive path 42. Conductive path 42 may be energized through any suitable means, such as through a use of wiring extending through the lumen 48 of tube 47 or any other suitable manner. While as shown in FIG. 6A, conductive path 42 extends only partially into the surface of substrate 41 used to form tube 47 in accordance with various other aspects of this embodiment of the present invention, path 42 may include a radial extension 49 which extends from lumen 48 to the outermost surface of tube as shown in FIG. 6B. In this manner, electrical connections can be made through the lumen. Alternatively, and in accordance with various other aspects of this embodiment of the present invention, connecting wires (not shown) may be passed along the exterior surface of tube 47.

While tubes 35 and 47 have been illustrated as including respective conductive paths 34 and 42 on the exterior portion of the tubes, those skilled in the art will appreciate that other configurations may suitably be formed. For example, the conductive paths may be formed on the interior portion of the tubes. Alternately, the conductive paths may be formed on the exterior portion of the tubes, such as shown in FIGS. 4 and 6, with such tubes thereafter being inverted (i.e., turned inside out) such that the conductive material is then oriented on the inside of the tubes. Similarly, the conductive paths may be formed on the interior of such tubes, and the tubes can be inverted such that the conductive paths are then oriented on the exterior of the tubes.

Figure 7:
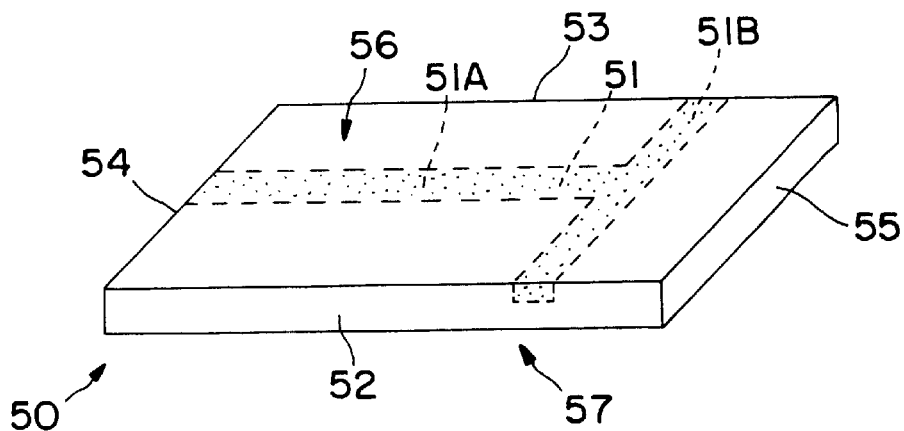
FIG. 7 is a perspective view of a further embodiment of a conductive surface in accordance with the present invention.

From the disclosure thus far provided, it should be appreciated that various conductive path configurations may be suitably provided in the various conductive surfaces of the present invention. Referring now to FIG. 7, a conductive surface 50 having a multi-component conductive path 51 may also be formed. As shown, conductive surface 50 suitably evidences a first edge 52, a second edge 53, a first end 54, and a second end 55. Further, surface 50 preferably evidences a top 56 and a bottom 57. In accordance with a preferred aspect of this embodiment, path 51 suitably includes portions 51A and 51B, wherein portion 51 A preferably runs substantially between edges 53 and 52 and portion 51B preferably runs between ends 55 and 54. Portions 51A and 51B are preferably electrically connected, such that, for example, current applied to portion 51A flows to portion 51B. As with the conductive portions of the various conductive surfaces previously described, conductive portions 51A and 51B are suitably formed by impregnating conductive particles into the body of surface 50. For example, with reference to FIGS. 8 and 8A, in accordance with one aspect of this embodiment of the present invention, portion 51A may extend throughout the thickness of surface 50, whereas portion 51B may extend only about a portion of the thickness of surface 50. It will be appreciated that various other combinations are also possible.

Conductive surface 50 may be suitably formed into a device, such as a tube 58 such as is shown in FIG. 9. Tube 58 is preferably formed by joining and attaching edges 53 and 52 of surface 50, such as by heat sealing or the like. As shown in FIG. 9, conductive path 51 may be configured on the exterior of tube 58, or as shown in FIG. 9B, on an interior portion of tube 59. As should be apparent, to form tube 59, edges 53 and 52 are joined and attached such that top 56 forms the central lumen of the tube.

With reference now to FIG. 9B, various other modifications in the configuration of conductive path 51 may be made. For example, as shown, portion 51B of conductive path 51 may not extend about the entire circumference of tube 58, but rather, portion 51B may extend only over a desired arc.

Figure 10:
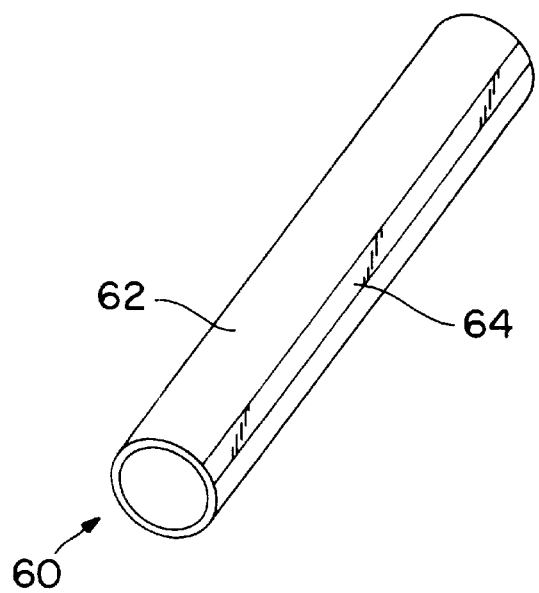
FIG. 10 is a perspective view of yet another embodiment of a tube formed of a conductive surface in accordance with the present invention.

While in connection with conductive surfaces 30, 40 and 50, the respective conductive paths have been described herein as being formed through the impregnation of conductive particles into the substrate, the conductive paths may be formed in any convenient manner. For example, the conductive paths may be applied to all or a portion of a tube-like structure. In this regard, and with reference now to FIG. 10, a tube 60 may be formed from a flexible material 62 and a conductive ribbon 64 attached thereto in any suitable manner. For example, ribbon 64 may be attached about its length to tube 60, or attached only as portions, or even, attached only at one end or one portion thereof. In accordance with a preferred aspect of this embodiment of the present invention, ribbon 64 is attached to material 62 by depositing ribbon onto material 62 or spot welding ribbon 64 to material 62. Although not shown in FIG. 10, ribbon 64 may extend beyond the length of tube 60. Preferably, in accordance with this aspect of the present invention, tube 60 is formed of a flexible substrate material, for example, of the type used to form tube 35.

Figure 11:
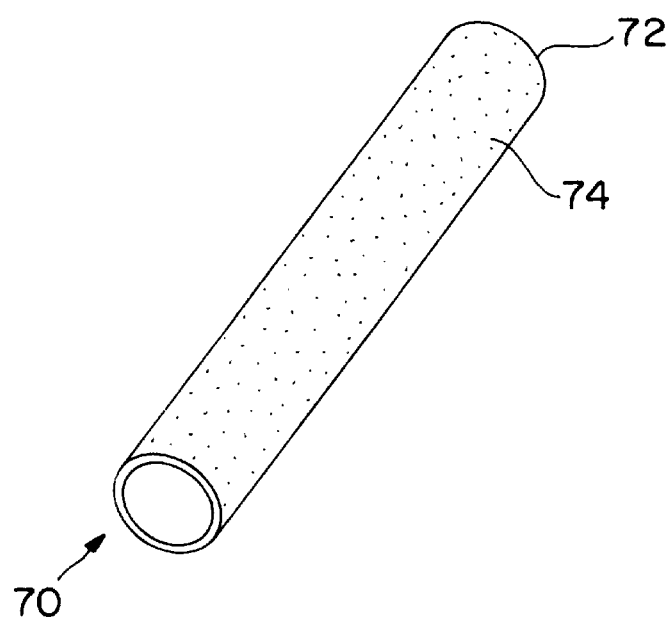
FIG. 11 is a perspective view of a still further embodiment of a tube formed of a conductive surface in accordance with the present invention.

In accordance with yet another embodiment of the present invention, a tube 70 shown in FIG. 11, is provided which is formed from a flexible material 72 fully impregnated with conductive particles 74. For example, flexible material 72 may be formed in a manner similar to that described hereinabove in connection with conductive layer 24 shown in FIG. 2.

The various tubes and conductive surfaces herein described can be used in a variety of manners in accordance with various aspects of the present invention. For example, one or more of the tubes may be used in connection with forming a probe for insertion into a body orifice. Various non-contaminating probes and methods of making and using the same are disclosed in the aforementioned '717 and '841 patents. Such probes may be configured for a variety of medical uses, such as a urinary catheter, a coronary catheter, a drainage tube, a medical probe, an introducer and/or the like. In any of those configurations, the unfolding membrane which enables the probe to be substantially non-contaminating can be provided with a conductive surface of the type described herein to offer additional advantages.

Referring now to FIGS. 12A and 12B, a probe 80, for insertion into a body orifice preferably includes a tube 81, an unfolding membrane 82, a conductive ribbon 83 and a guide ring assembly 84.

As shown, preferably a major portion of membrane 82 and conductive ribbon 83 are initially disposed inside the lumen of tube 81 with a minor portion of such materials extending outwardly over the leading edge of tube 81, the portions extending outside of tube 81 being attached to guide ring assembly 84. As shown, preferably ribbon 83 is suitably attached to a power supply 85, which power supply enables current or other electrical energy to be passed through to conductive ribbon 83. With reference to FIG. 12B, as probe 80 is inserted into a body orifice, for example, the urethral canal of a human or animal, or a body port or other orifice, membrane 82 and conductive ribbon 83 are suitably unfolded out of tube 81 and disposed along the outside surface of tube 81 interposed between tube 81 and the body orifice.

Inasmuch as the use and operation of probes 80 such as are briefly described herein are described in greater detail in connection with the aforementioned '717 and '841 patents, they will not be further described in this application.

Figure 13:
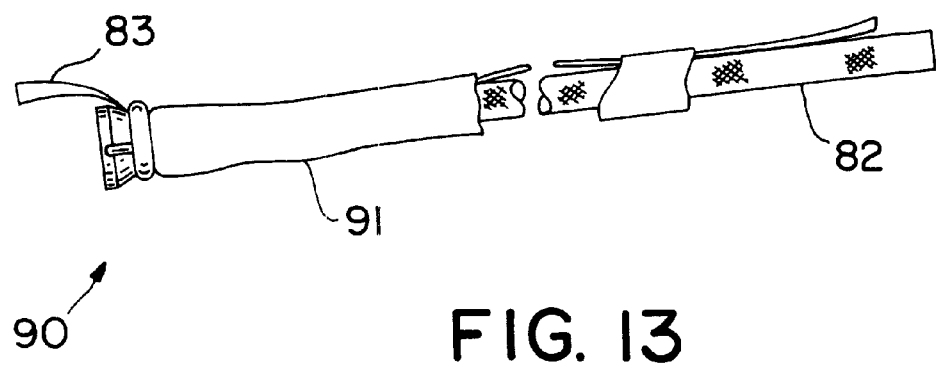
FIG. 13 is a perspective view of a further embodiment of a probe in accordance with the present invention.

Various other probe-type configurations can also be formed. With reference now to FIG. 13, a probe assembly 90 for use in connection with a tube 81 may be further provided with an external sheath material 91 which is attached over membrane 82 and ribbon 83. Such a protective sheath may further provide protection of ribbon 83 and/or provide a barrier between ribbon 83 and the body orifice. Assembly 90 can be used in connection with a tube 81 in a manner similar to that described in connection with probe 80 shown in FIGS. 12A and 12B.

Figure 14:
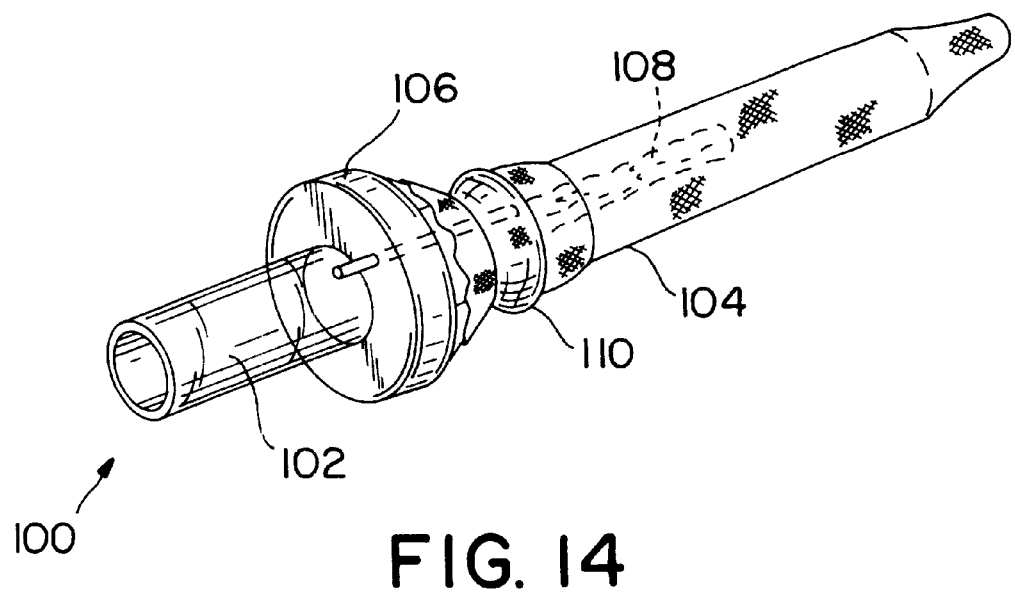
FIG. 14 is a perspective view of a still further embodiment of a probe in accordance with the present invention.

The various conductive surface materials in accordance with various aspects of the present invention may also be used in connection with the formation of a variably inflatable medical device, such as that as shown in U.S. Pat. No. 5,676,688. Specifically, the non-contaminating surgical introducer/dilator disclosed in the '688 patent includes a variably inflatable tubular balloon membrane. In connection with the present invention, the tubular balloon membrane may be formed of a conductive surface material, for example, such as described in connection with FIGS. 4, 6, 8, and/or 10. Alternatively, and as shown in FIG. 14, a conductive ribbon may be placed interiorly of the double-walled balloon membranae useful in connection with that particular device. As shown in FIG. 14, a non-contaminating device 100 preferably includes an introducer tube 102, a membrane 104, a guide 106, a conductive ribbon 108, and a retaining device 110. As shown, membrane 104 preferably comprises a double tube configuration including an inner tube and an outer tube. Ribbon 108 is preferably placed between inner tube and outer tube or alternatively may be placed along the external surface of the tube, which is caused to unfold through use of introducer/dilator 100.

It should be appreciated that other probe configurations also may be formed in accordance with various aspects of the present invention. From the description herein provided, various modifications and other configurations will likely be apparent to those skilled in the art. The previous probe examples have been provided for illustrative purposes only and not as a limitation of the type of probe which can be formed in accordance with the present invention. In general, in any case wherein which a conductive surface can be useful, aspects of the present invention may be employed.

The various conductive surface materials herein described may also be utilized to form additional devices.

With reference now to FIG. 15, a conductive surface of the type shown in FIG. 5 may be joined to a non-conductive surface or yet another conductive surface to form a pouch 110. As shown, pouch 110 preferably includes a first material 111 and a second material 112. Materials 111 and 112 are suitably joined along three sides thereof, such as by heat sealing, to form an edge 113 that extends therearound. As shown, sheet 111 may be suitably provided with a conductive path 115. Conductive path 115, when suitably connected to an appropriate power supply or other activation source, may be suitably utilized to heat or otherwise send an electrical charge to the materials contained within pouch 110. Various uses of such a configuration will be apparent to those skilled in the art.

Various other devices may be formed of the conductive surface materials herein described. For example, the various devices which are disclosed in co-pending U.S. patent application Ser. No. 08/911,496 by the same inventors may be augmented with the conductive surface materials disclosed herein. Exemplary devices are discuses herein below.

Referring now to FIG. 16, a tube 120 in accordance with a further embodiment of the invention may be formed of four layers of material, namely respective layers 121, 122, 123 and 124, one or more of which may comprise a conductive surface material in accordance with the present invention. Preferably, layers 121, 122, 123 and 124 are suitably sealed at, for example, respective edges 125 and 126 to form longitudinal seals about the length thereof. Such seals are suitably formed by, for example, heat-sealing as described hereinabove. As will be readily appreciated from FIG. 16, tube 120 provides a lumen between adjacent layers of material, namely a lumen 127 between juxtaposed layers 121 and 122, a lumen 128 between juxtaposed layers 122 and 123, and a lumen 129 between juxtaposed layers 123 and 124. In accordance with a particularly preferred aspect of this embodiment of the present invention, one (or more) of the layers is suitably provided as a conductive surface. For example, surface 121 may include a conductive path 130 provided along a length thereof. It should be appreciated that various configurations of multi-lumen tubes having one or more layers formed in whole or in part of a conductive surface material in accordance with the present invention may be made, and thus are within the scope of the present invention.

In accordance with various other embodiments of the present invention, the conductive surface materials disclosed herein may be suitably used as coverings and/or coatings for various other devices. For example, in the context of various surgical applications, stents are used to separate tissues, organs or other members for a variety of medical purposes. Such stents may be formed of plastic, metal or other materials and may exhibit a multitude of configurations. In accordance with various aspects of these embodiments of the present invention, the conductive surface materials disclosed herein are useful in covering such stents to render them more useful and offer significant advantages over currently available stents.

Referring now to FIG. 17, a stent structure 140, suitably comprising a frame member 142, typically formed of wire or other material, is configured to exhibit a number of openings and preferably is wound into a bundle, the bundle being covered by a conductive surface material 144 in accordance with the present invention. Membrane material 144 may be suitably secured to member 142 by, for example, wrapping material 144 around the end of the stent and heat-sealed upon itself to suitably secure that end of the membrane material to the end of the stent. Alternatively, a tab configuration (not shown) can be formed in the piece of material to attach the material to the stent. Material 144 is provided with a conductive path 146, which when activated may provide heat to that portion of the stent.

Figure 18:
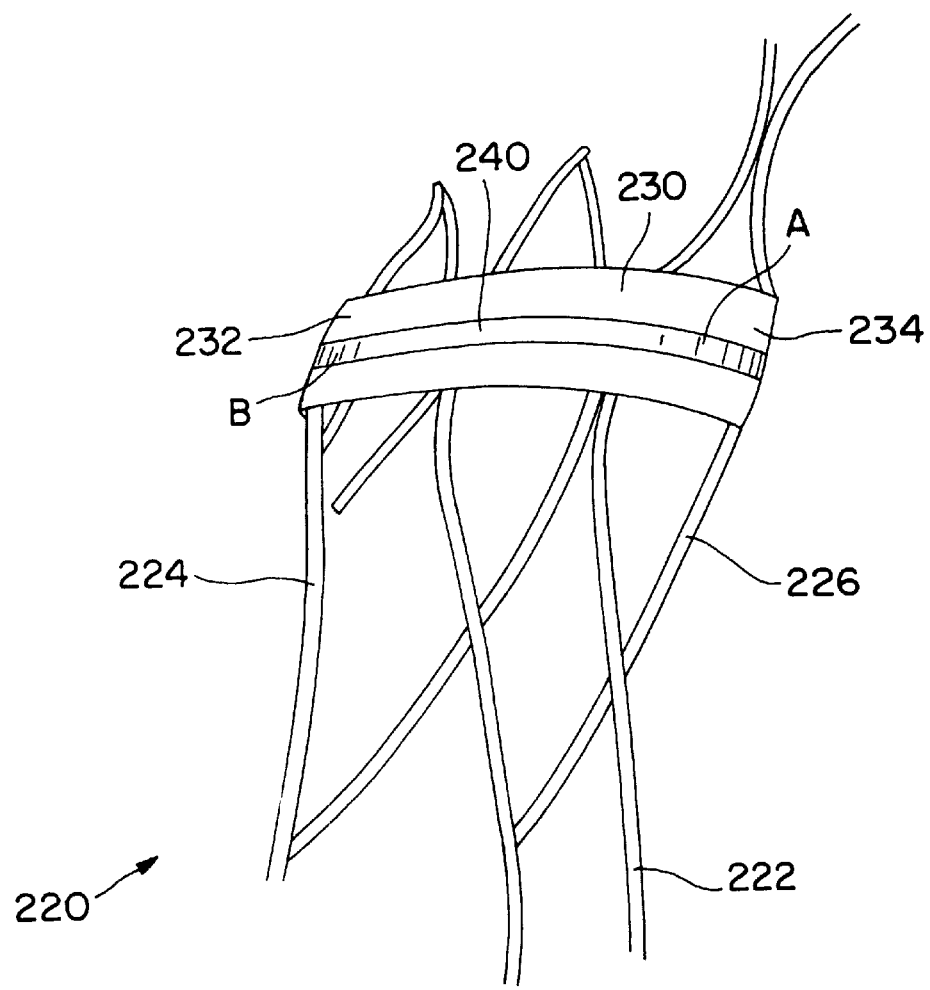
FIG. 18 is a perspective view of a further embodiment of the conductive surface in accordance with the present invention used as a stent covering.

Alternative stent covering configurations may also be employed in connection with the present invention. Referring now to FIG. 18, a further embodiment of a stent covering in accordance with the present invention is shown. For example, a suitable stent structure 220 is formed by a frame 222 optimally configured to exhibit a plurality of openings. Frame 222, as shown, includes at least a first end frame member 224 and a second end frame member 226. In accordance with this aspect of this embodiment of the present invention, a suitably sized and dimensioned piece of conductive surface membrane material 230 having a first end 232 and a second end 234 is suitably wrapped around stent frame 222. Preferably, and as shown in FIG. 18, first end 232 is suitably wrapped around member 224; similarly, second end 234 is suitably wrapped around member 226. Preferably, the respective ends of sheet 230 are suitably sealed to secure sheet 230 to stent frame 222. While various securement techniques may be used, spot welding techniques, such as through the application of heat at a particular spot along sheet 230 suitably are used. For example, as shown in FIG. 18, end 234 is tucked under frame member 226 and a suitable spot weld may be applied at point A. Similarly, end 232 is wrapped around member 224 and may be preferably folded back over itself and then spot-welded, for example, at location B to securely hold end 232 to stent frame 222. Conductive surface membrane material 230 is suitably provided with a conductive path 240 which extends about the length of material 230 suitably about and around stent frame 222. Activation of path 240 suitably causes heating of the region and thus of the sent.

Figure 19:
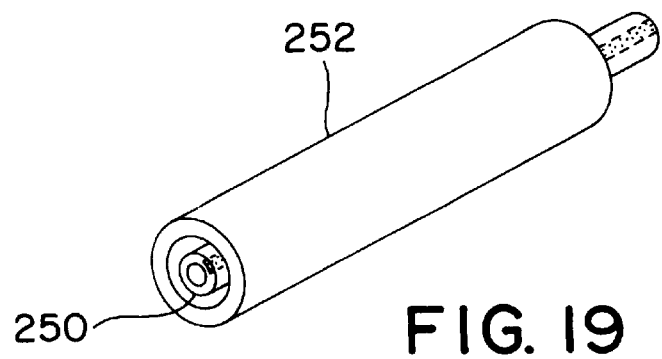
FIG. 19 is a perspective view of a tube formed of the conductive surface in accordance with the present invention which is part surrounded by a further protective sheath.

Various other configurations may be formed of the conductive surface materials disclosed herein. For example, various flexible tubes may be combined for certain purposes. For example, with reference now to FIG. 19, a conductive tube 250, of the type shown in FIG. 10, may be provided with a protective sheath as shown. Sheath 252 preferably comprises a flexible material, preferably a PTFE resin material which may be provided in the form of a conductive or non-conductive sheath. For example, sheath 252 may be formed of a conductive surface material such as layer 24 set forth in FIG. 2. Alternatively, sheath 252 may be non-conductive and be simply used in connection with conductive tube 250. It will be understood that the above description is of preferred exemplary embodiments of the present invention, and that the invention is not limited to the specific forms shown and described herein. For example, some or all of the components may be modified and alternative configurations which are apparent to those skilled in the art can be made and some various modifications may be made in the design and arrangements of the elements within the scope of the present invention as expressed in the appended claims.

Various configurations and medical devices disclosed herein as being in accordance with the present invention are shown for illustration only, and are not meant to limit the configurations or applications of the present invention to any particular manner.

We claim:

1. A probe for insertion into a body orifice comprising:

a tube having first and second open ends;

a polytetrafluoroethylene membrane, said membrane having a first end and a second end, wherein said first end of said membrane is interior of said tube and said second end of said membrane exterior said tube;

a conductive ribbon proximate to said membrane; and a guide assembly connected to said membrane;

wherein said membrane and said ribbon are inverted over said first open end of said tube.

2. A probe system useful for inserting a probe into a body cavity, said system comprising:

a probe having first and second ends and a hollow body spanning therebetween;

an unfolding sheath comprising a polytetrafluoroethylene resin, said sheath having first and second ends, said second end of said sheath initially contained within said hollow body of said probe, said sheath further being provided with a conductive path, said sheath configured such that when said probe is inserted into the body cavity, said sheath is withdrawn from said hollow body and interposed between the cavity and said probe along an exterior of said probe as said probe is inserted into the cavity, and a guide attached to said first end of said sheath, said guide and first end being disposed about the exterior of said probe first end.

3. The probe of claim 2 wherein said conductive path is provided longitudinally along the length of said sheath.

4. The probe of claim 2 wherein said conductive path is provided circumferentially around a portion of said sheath.

5. The probe of claim 2 wherein said conductive path comprises a substantial portion of said sheath.

6. The probe of claim 2 wherein said conductive path comprises a conductive material attached to a portion of said sheath.

* * * * *